(12) United States Patent
Nguyen et al.

(10) Patent No.: US 11,857,161 B2
(45) Date of Patent: Jan. 2, 2024

(54) CHAMBERED HANDLE FOR A MEDICAL DEVICE

(71) Applicant: Boston Scientific Scimed, Inc., Maple Grove, MN (US)

(72) Inventors: Man Minh Nguyen, Harvard, MA (US); Thomas Jeffrey Miller, Issaquah, WA (US); Maria Therese Maillet, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 127 days.

(21) Appl. No.: 16/862,673

(22) Filed: Apr. 30, 2020

(65) Prior Publication Data

US 2020/0345207 A1   Nov. 5, 2020

Related U.S. Application Data

(60) Provisional application No. 62/841,377, filed on May 1, 2019.

(51) Int. Cl.
| | |
|---|---|
| *A61B 1/005* | (2006.01) |
| *A61B 1/00* | (2006.01) |
| *A61B 1/05* | (2006.01) |
| *A61B 1/06* | (2006.01) |

(52) U.S. Cl.
CPC ........ *A61B 1/0052* (2013.01); *A61B 1/00009* (2013.01); *A61B 1/0011* (2013.01); *A61B 1/00068* (2013.01); *A61B 1/00119* (2013.01); *A61B 1/05* (2013.01); *A61B 1/0676* (2013.01)

(58) Field of Classification Search
CPC ............ A61B 1/00066; A61B 1/00068; A61B 1/0052
See application file for complete search history.

(56) References Cited

U.S. PATENT DOCUMENTS

| | | | |
|---|---|---|---|
| 6,716,160 B2* | 4/2004 | Mitsumori | A61B 1/005 600/131 |
| 2004/0193011 A1* | 9/2004 | Akiba | A61B 1/0052 600/122 |
| 2007/0299303 A1 | 12/2007 | Ogikubo | |
| 2009/0187146 A1 | 7/2009 | Landman et al. | |
| 2014/0200513 A1* | 7/2014 | Koitabashi | A61B 1/0055 604/95.04 |
| 2016/0367112 A1* | 12/2016 | Koyama | A61B 1/0052 |
| 2017/0265719 A1* | 9/2017 | Koyama | A61B 1/00 |
| 2018/0192857 A1 | 12/2018 | Grant et al. | |
| 2019/0313881 A1* | 10/2019 | Francher | A61B 1/00105 |
| 2019/0350440 A1* | 11/2019 | Leong | A61B 1/0057 |

FOREIGN PATENT DOCUMENTS

| | | |
|---|---|---|
| EP | 3207854 A1 | 8/2017 |
| WO | 2018058007 A1 | 3/2018 |

* cited by examiner

*Primary Examiner* — Alexandra L Newton
(74) *Attorney, Agent, or Firm* — Bookoff McAndrews, PLLC

(57) ABSTRACT

A handle of an endoscope may comprise a body portion that defines a first chamber having a first feature configured to support at least a first component of a steering assembly, and a second chamber having a second feature configured to support at least one fluidic component or electronic component.

17 Claims, 5 Drawing Sheets

CHAMBERED HANDLE FOR A MEDICAL DEVICE

CROSS-REFERENCE TO RELATED APPLICATIONS

This application claims the benefit of priority from U.S. Provisional Application No. 62/841,377, filed on May 1, 2019, which is incorporated by reference herein in its entirety.

TECHNICAL FIELD

The present disclosure relates generally to handles of medical devices, including endoscopes.

BACKGROUND

Endoscopes or other medical devices may include a handle portion, which may be gripped by an operator and may include control elements for functions such as steering, suction, water (e.g., irrigation), air, light, and imaging. An endoscope may also include a portion which may be inserted into a subject. For example, an endoscope may include an elongate tube suitable for insertion into a subject. Such an insertion portion of an endoscope may include one or more lumens. The lumens of an insertion portion of an endoscope may support functions, for example, conveying air, water, suction, electricity, data, light, and/or images. Tools may also be inserted via a working channel of an insertion portion of an endoscope. For example, a tool may be inserted through a port in or near the handle of an endoscope.

Handles of such devices may house multiple components. Such components may need to be placed in particular locations within the handle. Placement of such components in handles has involved the use of support components that are separate from a handle shell and that are inserted into the handle in order to provide a frame or other suitable structure within the handle for housing components. Such frames or support structures may increase manufacturing costs by increasing the number of parts in the medical device and by requiring resources for assembling the frames or structures within the handle. These manufacturing costs may impair production of disposable devices. Therefore, a need exists for handles of endoscopes, or other medical devices, which are manufactured with efficient techniques and which satisfy the requirements for using the device in a subject.

SUMMARY

In one example, a handle of an endoscope may comprise a body portion that defines a first chamber having a first feature configured to support at least a first component of a steering assembly, and a second chamber having a second feature configured to support at least one fluidic component or electronic component.

Any example of handles of endoscopes described herein may have a body portion with a first surface on a first side of a longitudinal axis of the body portion and a surface on a second side of a longitudinal axis of the body portion. The first surface may define at least part of the second chamber. The second surface may define at least part of the first chamber. The body portion further may further define a recessed portion proximal of the first chamber and configured to receive at least a second component of the steering assembly. At least one wall may surround the recessed portion. The wall may have at least a curved portion and a straight portion. The second chamber may include a negative of the recessed portion. The recessed portion may define a first recessed portion and a second recessed portion. The second recessed portion is recessed from the first recessed portion. The second recessed portion may be configured to receive at least a third component of the steering assembly. The second chamber may have a third feature configured to support at least one valve body. The wall of the second chamber includes a concave portion configured to surround at least a portion of the valve body. The second feature may be configured to support at least one electronic component, wherein the electronic component is a circuit board, and wherein the second chamber has a third feature configured to support a button that is operatively connected to the circuit board. The first chamber and the second chamber may be in fluid communication with one another. A passage between the first chamber and the second chamber may include a feature configured to constrain a tube or a wire passing between the first chamber and the second chamber. A first cover may be attached to the body portion to enclose the first chamber, and the second cover may be attached to the body portion to enclose the second chamber. The body portion may further include a feature configured to receive a port in fluid communication with a working channel. The first chamber may be open on one side of a longitudinal axis of the body portion. The second chamber may be open on a second, opposite side of the longitudinal axis of the body portion;

In another example, a handle of an endoscope may comprise a main body portion defining a first chamber and a second chamber. The first chamber may be open on one side of a longitudinal axis of the main body portion. The second chamber may be open on a second, opposite side of the longitudinal axis of the main body portion. A component of a steering assembly may be disposed in the first chamber. At least one of a fluidic component or an electronic component may be disposed in the second chamber. A first cover may be over the first chamber. A second cover may be over the second chamber.

Any example of handles of endoscopes described herein may have any of the following features. The first chamber may include a first feature configured to support the component of the steering assembly. The second chamber may include a second feature configured to support the at least one of the fluidic component or the electronic component. The component of the steering assembly may be a first component of the steering assembly. The main body portion may define a recessed portion proximal of the first chamber and may be configured to receive at least a second component of the steering assembly. The at least one of the fluidic component and the electronic component may be the electronic component, and the handle may further comprise a button operatively connected to the electronic component, and wherein the second chamber includes a feature configured to support the button. The first chamber and the second chamber may be in fluid communication with one another. The first cover may be attached to the main body portion to enclose the first chamber. The second cover may be attached to the main body portion to enclose the second chamber.

In yet another example, a handle of an endoscope may comprise a body portion that includes: a first wall that defines (a) a first exterior surface of the handle and (b) a first chamber configured to receive at least one steering component; and a second wall that defines (a) a second exterior surface of the handle and (b) a second chamber configured to receive at least one of a fluidic component and an electronic component. The first wall and the second wall may be on opposite sides of a longitudinal axis of the body portion. The first chamber may include a first feature configured to support the component of the steering assembly. The second chamber may include a second feature configured to support the at least one of the fluidic component and the electronic component. The second chamber may include a third feature configured to support at least one valve body.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator. Although endoscopes are referenced herein, reference to endoscopes or endoscopy should not be construed as limiting the possible applications of the disclosed handles and other aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Operational portions of endoscopes (e.g., handle portions of endoscopes) may include a variety of components that are used by an operator when performing a procedure with the endoscope. For example, an operational portion of an endoscope may include steering components used to deflect a distal portion of an insertion portion of the endoscope. The operational portion may also include electronics for operating, for example, a camera or lighting in a distal portion of an endoscope, or for transferring image data. The operational portion may also include fluidic components, such as valves and tubing for air, water, suction, and/or instruments. Furthermore, the operational portion may include mechanisms for raising or lowering an elevator at a distal end of an endoscope. Any or all of these components fit within an operation portion, such as a handle, in a manner suitable to perform the functions and provide the necessary connections therebetween and to external components. Certain of these components should be kept separate from one another so as to avoid interference with the components, fluid leakage, etc. This disclosure describes, for example, a handle of an endoscope that contains built-in features and structures for supporting, segregating, aligning, or otherwise positioning components, such as those described above, that may reside in the handle. Such a handle may minimize manufacturing costs by reducing a number and cost of parts and/or by reducing the number of steps, time, and difficulty involved in manufacturing.

Figure 1:
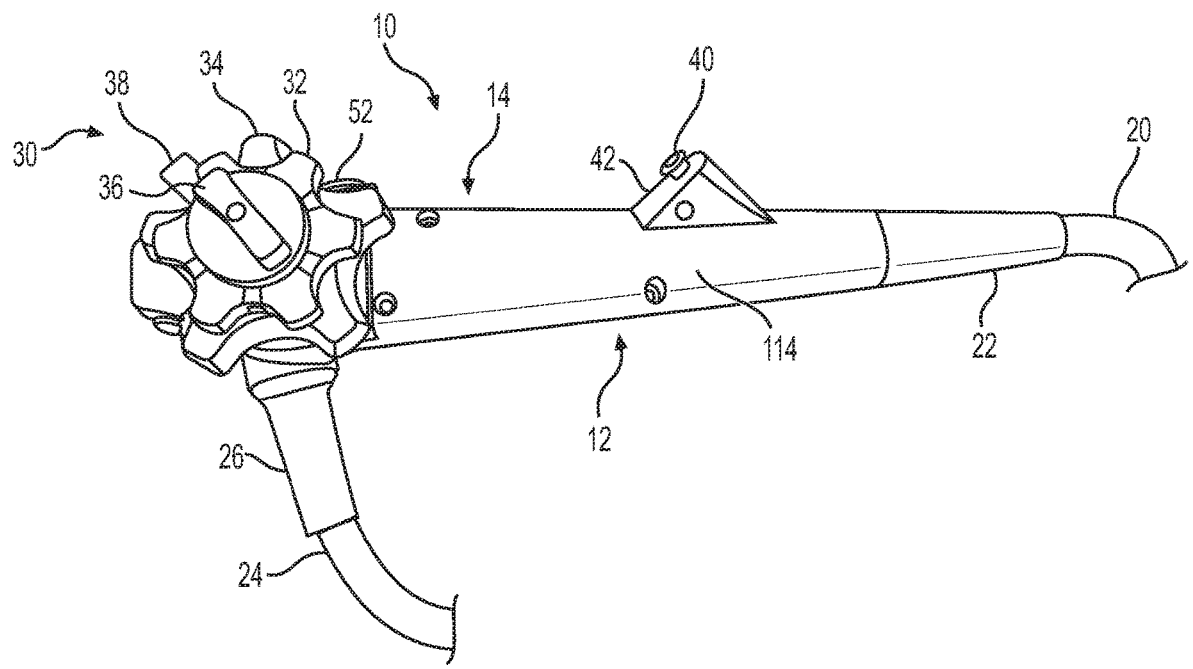
FIGS. 1-2 show perspective views of a medical device.
Figure 2:
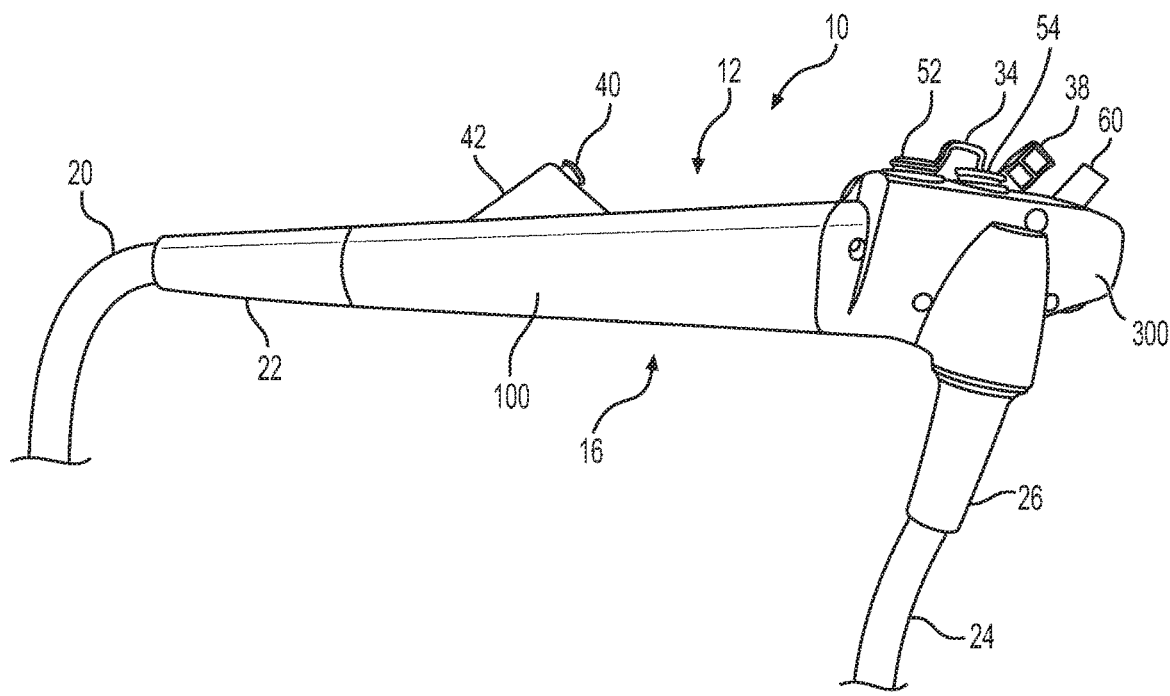

FIGS. 1 and 2 depict an exemplary device 10. Device 10 may have an operation portion 12, which may have a first side 14 (see FIG. 1) and a second side 16 opposite first side 14 (see FIG. 2). Device 10 may be an endoscope, duodenoscope, bronchoscope, ureteroscope, colonoscope, or other type of medical device. Device 10 may also include an insertion portion 20, which may be inserted into a body lumen of a subject during a medical procedure. Insertion portion 20 may be joined to operation portion 12. A stress relief portion 22 may bridge operation portion 12 and insertion portion 20. An umbilicus 24 may extend from operation portion 12, and a stress relief portion 26 may bridge operation portion 12 and umbilicus 24. Umbilicus 24 may be used to connect device 10 to components, such as a controller (for providing, e.g., optical controls including camera, video, light, or other optical controls), an air and/or water supply, and/or a suction supply.

Operation portion 12 may include a number of components used by an operator to control device 10 before, during, or after a procedure involving device 10. For example, operation portion 12 may include steering components 30. Steering components 30 may be used to control deflection of a distal portion (not shown) of insertion portion 20. Steering components 30 may be a part of a steering assembly. For example, steering components 30 may include two knobs, 32, 34, used for deflecting a distal portion of insertion portion 20. For example, one of knobs 32, 34 may be used to deflect a distal portion of insertion portion 20 in a left/right direction, and the other of knobs 32, 34 may be used to deflect a distal portion of insertion portion 20 in an up/down direction. For example, knob 32 may be operable to deflect a distal portion of insertion portion 20 in a left/right direction, and knob 34 may be operable to deflect a distal portion of insertion portion 20 in an up/down direction. Steering components 30 may also include locking mechanisms 36, 38, which may be used so as to limit a distal portion of insertion portion 20 from moving in a left/right and/or up/down direction or otherwise lock the position of the distal portion. For example, locking mechanism 36 may be a knob that is operable to prevent knob 32 from deflecting a distal portion of insertion portion 20 in a left/right direction. Locking mechanism 38 may be a lever that is operable to prevent knob 34 from deflecting a distal portion of insertion portion 20 in an up/down direction.

Operation portion 12 may also include a number of ports and/or valves. For example, operation portion may include a working channel port 40 that may be used for passing instruments or other devices down a working channel of insertion portion 20. Working channel port 40 may be housed in a port housing 42. Port 40 may include a valve to prevent leakage. Operation portion 12 may also include fluidic components, such as valves 52, 54 for providing air, water, and/or suction. Valves 52, 54 may connect to tubing in umbilicus 24, operation portion 12, and/or insertion portion 20, such that pressing on valves 52, 54 permits the corresponding function. For example, valve 52 may be used to provide air and/or water. Valve 54 may be used to provide suction and may connect to a working channel extending from working channel port 40.

Operation portion 12 may also include other components such as elevator lever 60, which may be used to move an elevator (not shown) at a distal end of insertion portion 20 up and/or down. For example, elevator lever 60 may be used where device 10 is a duodenoscope.

Figure 3:
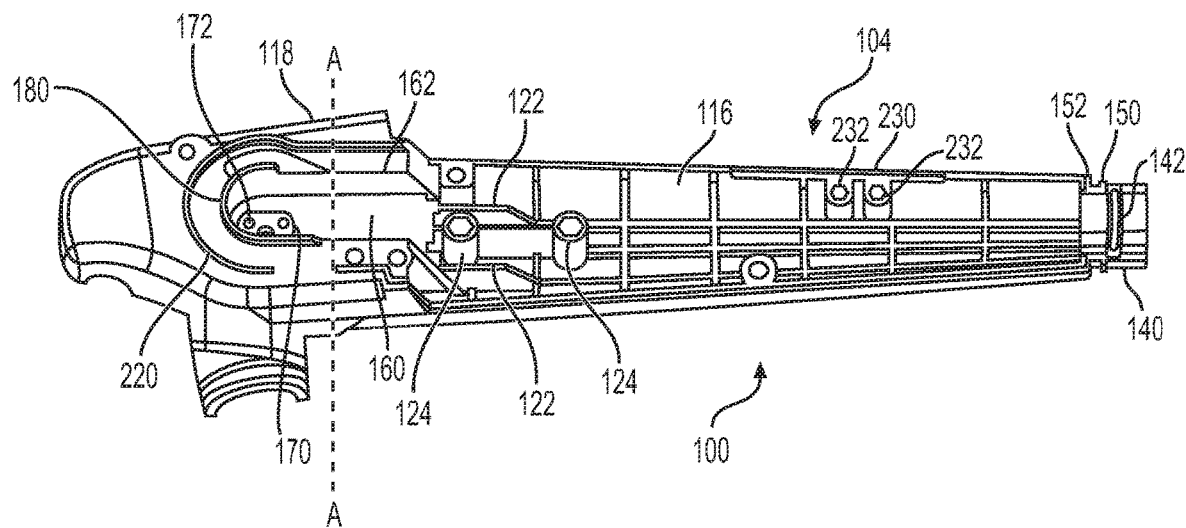
FIGS. 3-4 show perspective views of a handle component of a medical device.
Figure 4:
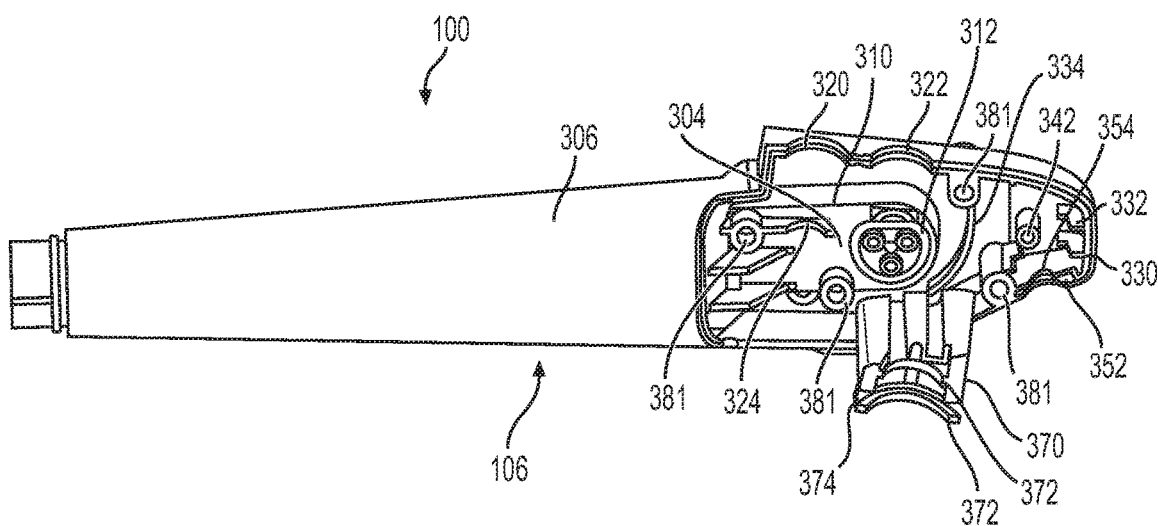

As shown in FIGS. 3 and 4, operation portion 12 may include a main body portion 100. Main body portion 100 may have a first side 104 (FIG. 3) and a second side 106 opposite first side 104 (FIG. 4). In some embodiments, the main body portion 100 may be one-piece. First side 104 of main body portion 100 may correspond to first side of 14 of operation portion 12. Second side 106 of main body portion 100 may correspond to second side 16 of operation portion 12. FIGS. 3 and 5-7 depict aspects of first side 14 of operation portion 12 and/or first side 104 of main body portion 100. FIGS. 2, 4, 8, and 9 depict second side 16 of operation portion 12 and/or second side 106 of main body portion 100. Main body portion 100 may be formed from rigid material, such as plastic or metal, or any other suitable material. Main body portion 100 may be formed of one integral structure and may be, for example, molded.

First side 104 of operation main body portion 100 may include features or structures for supporting, segregating, and/or positioning certain components installed in operation portion 10. For example, components which interact with steering components 30 and/or elevator lever 60 may be positioned alongside first side 104 of operation main body portion 100, within recessed portions of first side 104 of operation main body portion 100, or otherwise interacting with first side 104 of operation main body portion 100.

Figure 5:
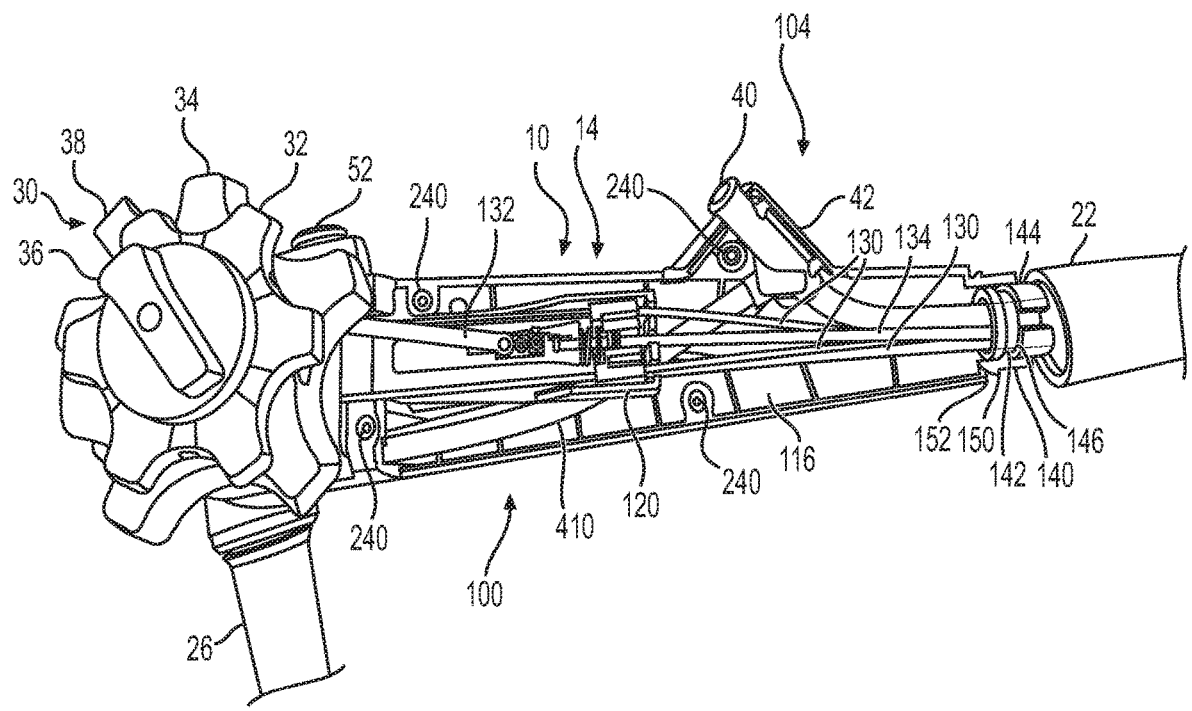
FIG. 5 shows a perspective view of a medical device with a cover portion removed.

FIG. 5 shows first side 14 of operation portion 10 and its corresponding components, with a first side cover portion 114 (see FIG. 7) removed. Stress relief portion 22 is shifted distally in FIG. 5 to better show the structure of body portion 100. Removal of first side cover portion 114 exposes some of the components that may be installed in operation portion 10. The portion of body portion 100 and housing that may be covered by cover portion 114 may form a first chamber 116 for receiving components. FIG. 5 does not show all components that may be installed in operation portion 10 and/or chamber 116 and should not be construed as limiting the components that could be installed or would be installed. First side 104 of operation main body portion 100 is also visible underlying the components. An outer surface of a first side 14 of operation portion 12 may be formed partially by cover portion 114 and partially by a wall 118 of first side 104 of main body portion.

Referring primarily to FIGS. 3 and 5, main body portion 100 may include a variety of features for supporting, positioning, or otherwise interacting with components of operation portion 10. For example, main body portion 100 may include support structures or features for receiving a steering block 120. Steering block 120 may be a component of a steering assembly, along with steering components 30. For example, main body portion 100 may include one or more walls 122 that align with and/or interact with portions of steering block 120. For example, walls 122 may align with outer edges of steering block 120 or may interact with indentations or grooves of steering block 120 to fix steering block 120 in place. Main body portion 100 may also include one or more features such a holes or cavities 124, which may be used for securing steering block 120. For example, cavities 124 may be configured to receive a screw or other securing mechanism to secure steering block 120 to main body portion 100. Cavities 124 may be, for example, threaded to receive a screw or may have a complementary, mating shape to a fixing mechanism. For example, as shown in FIG. 3, cavities 124 have a hexagonal shape. A fixing mechanism for fixing steering block 120 to main body portion 100 may have a corresponding hexagonal shape to fit within cavities 124 with a mating shape. Alternatively, any other mechanisms could be used for fixing steering block 120 to main body portion 100. As another alternative, steering block 120 could be formed integrally with main body portion 100. The design of main body portion 100 may allow for mounting of steering mechanisms (including steering block 120 or steering components 30) directly to main body portion 100, rather than to additional internal support component(s).

Steering block 120 may have features to provide support for steering wires 130, which may interact with steering components 30 to deflect a distal end of insertion portion 20. Steering block 120 may also house or otherwise connect to components such as an arm 132 and a pull wire 134 for raising and/or lowering an elevator at a distal end of insertion portion 20. Alternatively, steering block 120 may be omitted, and portions of main body portion 100 may provide support, structure, stability, etc. for components such as steering wires 130, arm 132, and/or pull wire 134. Alternatively, any other suitable steering mechanisms may be used and may interact with features of main body portion 100 in order to position the steering mechanisms.

Main body portion 100 may also include a feature such as a distal neck portion 140 that is smaller in cross-section than a more proximal portion of main body portion 100. Neck portion 140 may include a raised ridge 142. A sleeve 144 formed of either flexible or rigid (e.g., plastic) material may include an annular groove 146 that mates with ridge 142. Components of operation portion 10 that will pass distally through insertion portion 20 may first pass through sleeve 144. An interaction between groove 146 and ridge 142 may help keep sleeve 144 in place. Stress relief portion 22 may fit over neck portion 140. Neck portion 140 may include a ridge 150 and/or a shoulder 152 to assist in keeping stress relief portion 22 in place on neck portion 140. For example, a proximal portion of stress relief portion 22 may fit between ridge 150 and shoulder 152, which will resist distal or proximal movement of stress relief portion 22.

Figure 6:
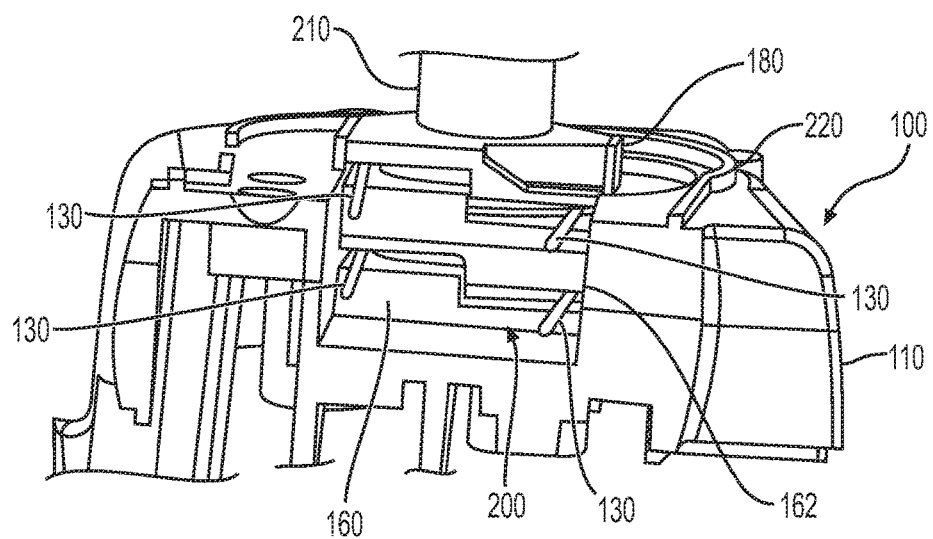
FIG. 6 shows a cross-sectional view of a portion of a medical device.

Now referring primarily to FIGS. 3 and 6, main body portion 100 may include a feature such as recessed portion 160. Recessed portion 160 may have walls 162 surrounding some but not all of recessed portion 160. Recessed portion 160 may be open on a distal end of recessed portion 160. Recessed portion may also be open along a side that is most radially outward from a longitudinal axis of main body portion 100. A longitudinal axis of the device is an axis extending along an operation portion and an insertion portion, and a longitudinal direction is a direction along the longitudinal axis. Alternatively, recessed portion 160 may have walls 162 surrounding entirety of recessed portion 160 or other subsets of recessed portion 160. Recessed portion 160 may have a rounded proximalmost side or end. The rounded side of recessed portion 160 may have a same or similar radius of curvature as an axle used in steering components 30 such that recessed portion 160 serves to support or constrain one or more steering components 30. For example, recessed portion 160 may include a semicircular proximalmost side. Other sides of recessed portion 160 may have straight-sided walls 162. For example, at a cross-section of main body portion 100 along line A-A, recessed portion 160 may have a rectangular cross-section, as shown in FIG. 6. For example, a curved (e.g., semicircular) side of recessed portion 160 may be a proximal side of recessed portion 160. Recessed portion 160 may include a further recessed portion 170, which may be more deeply recessed than recessed portion 160. Further recessed portion 170 may have one or more holes 172. For example, further recessed portion 170 may have one, two, three, or more holes 172. Further recessed portion 170 may be generally round in shape and may have a straightened edge on one or more sides.

Walls 162 may have a uniform height or may have a varying height measured along an axial direction of main body portion 100 (a direction perpendicular to a longitudinal direction of main body portion 100). For example, a ridge 180 may extend around a portion of a perimeter of recessed portion 160. For example, a ridge 180 may extend around a proximal, curved side of recessed portion 160. Ridge 180 may also extend along part of a straight side of recessed portion 160. For example, ridge 180 may extend along a part of a straight side of recessed portion 160 that is more proximate to umbilicus 24.

As shown in FIG. 6, a cable system 200 used for steering a distal end of insertion portion 24 may fit within recessed portion 160. Cable steering system 200 may have a complementary shape to recessed portion 160 so that cable steering system 200 fits securely within recessed portion 160. Use of recessed portion 160 may eliminate a need for a separate frame to position cable steering system 200. Further details of cable steering system 200 are described in concurrently filed U.S. Provisional Patent Application No. 62/841,290, titled "Systems and Devices for Articulation Wire Guidance, ", incorporated herein in its entirety. Cable steering system 200 may be used to transmit a force from steering components 30 to articulation wires 130, which may be another component of a steering assembly. For example, one or more of steering components may cause rotation of an axle, such as axle 210. Rotation of axle 210 may cause rotation of one or more spools and/or pulleys that are included in steering system 200. One or more components of cable steering system 200 or steering components 30 may also engage with further recessed portion 170. For example, a pulley, washer, axle, or other component of steering system 200 or steering components 30 may engage with further recessed portion 170 or holes 172. Holes 172 may be used to secure a component of steering system 200 to main body portion 100. Axle 210 of steering components 30 may be fixed to main body portion 100 via further recessed portion 170 and/or holes 172. For example, a base of axle 210 may have a complementary shape to recessed portion 170, such that recessed portion 170 may be used to locate axle 210 relative to body portion 100 and/or to constrain rotational movement of a base of axle 210 relative to body 100. Axle 210 may have a same or similar radius to a rounded portion of recessed portion 160 so that axle 210 fits within a rounded portion of recessed portion 160.

Body portion 100 may also include further features such as an outer ridge 220. Outer ridge 220 may have a shape similar to ridge 180. For example, at least part of outer ridge 220 may be curved. For example, at least a part of outer ridge 220 may form a partial circumference of a circle. Another part of outer ridge 220 may be straight. For example, a part of outer ridge 220 that is further from umbilicus 24 may be straight. While a straight portion of ridge 180 may extend distally on one side (e.g., a side closer to umbilicus 24) of recessed portion 160, a straight portion of ridge 220 may extend distally on the other side (e.g., further from umbilicus 24) of recessed portion 160. A straight portion of outer ridge 220 may extend further in a distal direction than a straight portion of ridge 180. Outer ridge 220 may have a greater radius of curvature than ridge 180.

Ridges 180 and/or 220 may be used to engage with components of steering components 30. For example, ridges 180 and/or 220 may be used to align a washer or other component of steering components 30. A height of ridge 180 may extend a height of walls 162 to reach a height of steering components 30, and ridge 220 may mate with portions of steering components 30.

Main body portion 100 may also include a feature such as portion 230 for engaging with port housing 42. For example, an edge of portion 230 may be slightly recessed from an edge of adjacent portions of main body portion 100. In other words, the outermost surface of portion 230 is recessed relative to adjacent outer surfaces of body portion 100. Portion 230 may also include one or more holes or cavities 232 for engaging connectors for coupling port housing 42 to main body portion 100. Cavities 232 may have any of the properties of cavities 124, discussed above.

Figure 7:
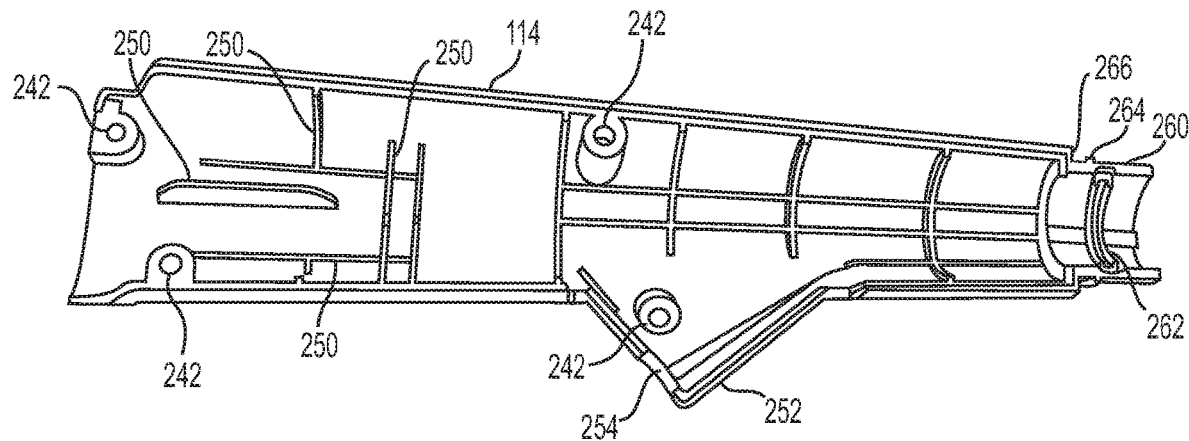
FIG. 7 shows a cover portion for a medical device.

FIG. 7 shows a first side cover portion 114 that has been removed from a first side 14 of operation portion 12, shown in FIG. 5. Cover portion 114 may be connectable to main body portion 100 by holes or recesses 240 in body portion 100 and corresponding holes or recesses 242 in cover portion 114. Cover portion 114 may fit over first chamber portion 116 and may fully or partially enclose first chamber 116. A mechanism such as a screw, pin, bolt, or other connector may be used to join holes or recesses 240 to holes or recesses 242. Additionally or alternatively, other mechanisms may be used for joining cover portion 114 to main body portion 100. For example, cover portion 114 may snap onto main body portion 100 or otherwise attach to main body portion, including, by glue, welding, or other adhesives. Cover portion 114 may include one or more protruding portions 250. Protruding portions may interact with components of device 10 (e.g., steering block 120 or other components) to position, support, activate, or secure the components. Cover portion 114 may include a port housing mating portion 252, which may have a complementary shape to port housing 42 and/or port 40. For example, port housing mating portion 252 may include a rounded indentation 254 with a same or similar radius of curvature as port 40 so that rounded indentation 254 fits around port 40 and secures port 40. Cover portion 114 may form a portion port housing 42, such as a portion of port housing 42 on first side 14 of operation portion 10.

Cover portion 114 may also include features such as a cover neck portion 260 that may have the same shape as or a complementary shape to neck portion 140 and that may align with neck portion 140 when cover portion 114 is secured to main body portion 100. Cover neck portion 260 may have a ridge 262 that may have any of the properties of ridge 142 and may interact with groove 262. Cover neck portion 260 may have a ridge 264 that may have any of the properties of ridge 150 and a shoulder 266 that may have any of the properties of shoulder 152. As with neck portion 140, stress relief portion may fit over cover neck portion 260. Together, neck portion 140 and cover neck portion 260 may have a circular cross-section and/or may form a tubular shape.

Figure 8:
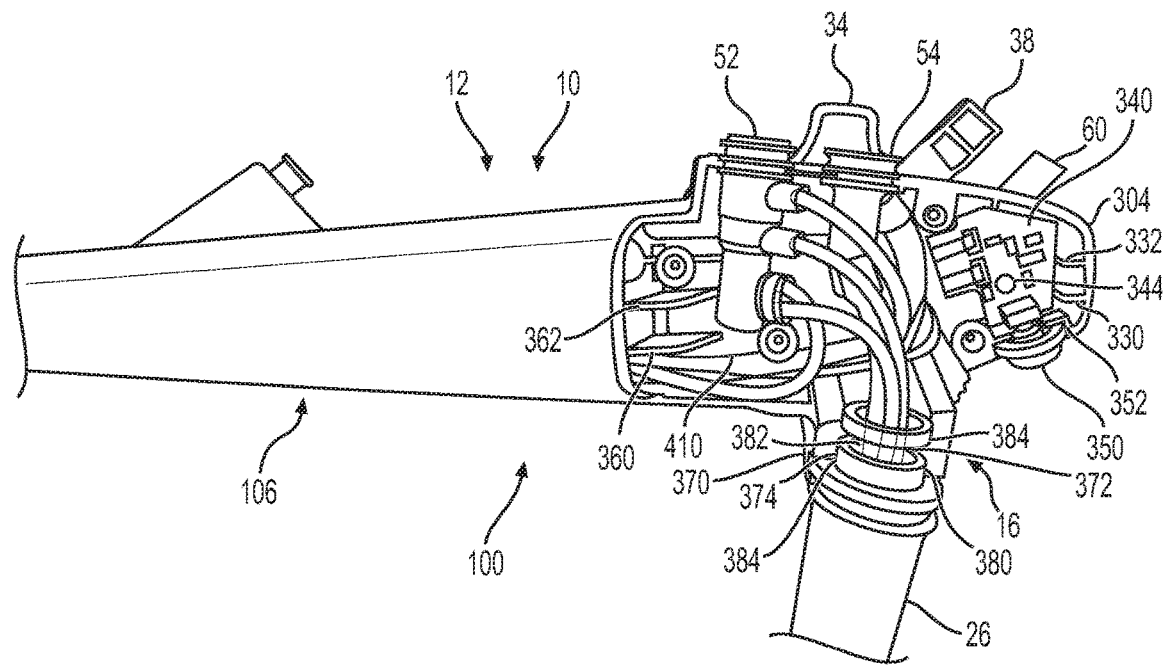
FIG. 8 shows a perspective view of a medical device with a cover portion removed.
Figure 9:
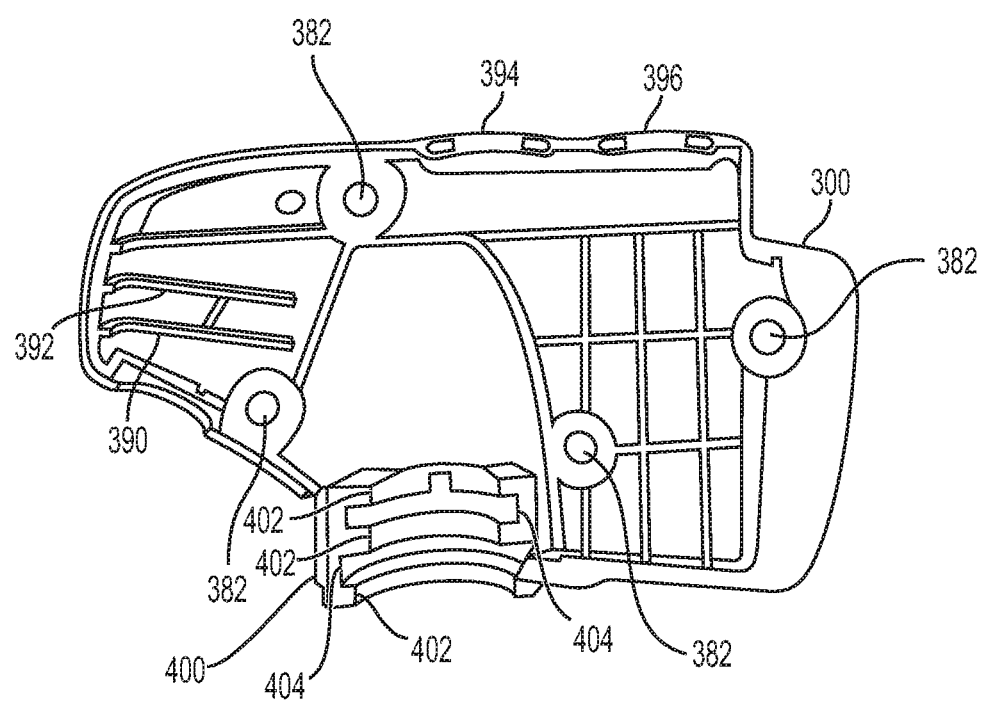
FIG. 9 shows a cover portion for a medical device.

FIGS. 4, 8, and 9 pertain to a second side 16 of operation portion 12. FIG. 4 shows a second, opposite side 106 of main body portion 100 from that shown in FIG. 3. FIG. 8 shows second side 16 of operation portion 12 with a second side cover portion 300 (see FIG. 9) removed. Removal of second side cover portion 300 exposes some of the components that may be installed in operation portion 10. FIG. 8 does not show all components that may be installed in operation portion 10 and should not be construed as limiting the components that could be installed or would be installed. Second side 106 of operation main body portion 100 is also visible underlying the components and toward a distal portion of main body portion 100. A portion of main body portion 100 that may be covered by cover portion 300 may form a second chamber 304 for housing components of operation portion 12.

An interior surface of second chamber 304 (that is, an outward facing surface of main body portion 100 that may be covered by cover portion 300) may be an opposite surface or side of wall 118. In other words, wall 118 may form or define an exterior of a first side 104 of a main body portion 100 and may form or define an interior of second chamber 304 on second side 106 of main body portion 100.

An outer surface of second side 16 of operation portion 12 may be formed partially by cover portion 300 and partially by a wall 306 of main body portion 100. An inner surface of wall 306 may define at least a portion of an interior of first chamber 116. In other words, wall 306 may form or define an exterior of a second side 106 of main body portion 100 and may form or define an interior of first chamber 116 on first side 104 of main body portion 100.

While first side cover portion 114 covers a more distal portion of main body portion 100, second side cover portion 300 covers a more proximal portion of body portion 100. The areas covered by first side cover portion 114 and second side cover portion 300 may or may not overlap on the opposite sides of body portion 100. In other words, a proximal portion of first chamber 116 and a distal portion of second chamber 304 may or may not overlap on opposite sides of body portion 100.

As can be seen in FIG. 4, second side 106 of operation main body 100 may include negatives of features from first side 114 of operation main body 100. For example, recessed portion 160 and further recessed portion 170 may form protrusions 310 and 312 on second side 106 of operation main body 100. Thus, structures from opposite sides of main body 100 may form structures from one another and may serve complementary or different functions on each side to provide structure within operation portion 10 in order to house components of device 10. Alternatively, a negative of a structure from one side may not serve a function on the other side. Such negatives may be formed because a surface of an exterior wall 118 forms an interior of second chamber 304, and a surface of an exterior wall 306 forms an interior of first chamber 116. Alternatively, interiors of first chamber 116 and second chamber 304 may have a shared wall.

Main body 100 may include features such as curved concave portions 320 and 322 in walls of main body 100 that have complementary shapes to bodies of valves 52 and 54. Outer surfaces of bodies of valves 52 and 54 may have a same or similar radius of curvature as concave portions 320 and 322. Main body 100 may include a further curved support portion 324 for supporting a body of valve 52. Support portion 324 may be shaped to be complementary to an outer surface of a body of valve 52 so as to support, position, or otherwise interact with a body of valve 52. For example, support portion 324 may protrude from adjacent surfaces of main body 100 and may have a radius of curvature similar to that of a portion of a body of valve 52 that will align with support portion 324. Valve 52 may be positioned and oriented in a manner such that it is ergonomic and constrained from movement that could cause damage to tubing within main body portion 100 (such as the tubing discussed below).

Main body portion 100 may also include features, such as protruding support portions 330, 332, and/or 334, for engaging an electronic component, such as a circuit board 340. Support portions 330, 332, and/or 334 may be shaped so as to engage edges of a circuit board 340 and/or otherwise support circuit board 340. Circuit board 340 may provide functionality to components such as lighting and camera components at a distal end of insertion portion 20. Circuit board 340 may be connected via wires to umbilicus 24 and insertion portion 20. Wires are not shown in FIG. 8 for clarity of illustration. Support portions 330, 332, and 334 may be formed integrally from the material forming main body portion 100. The presence of support portions 330, 332, and 334 may eliminate or limit a need for separate structural support components for supporting circuit board 340. Main body portion 100 may include a hole or cavity 342 that may be used for securing circuit board 340 to main body portion 100. For example, a screw 344 may pass through a hole in circuit board 340 and into cavity 342. Cavity 342 may have any of the properties of cavities 124, described above.

A button 350 may be accessible from an exterior of operation portion 12. Button 350 may be operatively coupled to circuit board 340 and may be used to activate functionality of electronic components of device 10. For example, button 350 may be operative, when pressed, to capture a still image picture from a camera at a distal end of insertion portion 20. As shown in FIG. 4, main body portion may include a slot 352 for receiving a base of button 350. A top inner side of slot 352 may include an indentation 354 for receiving a connector for connecting button 350 to circuit board 340. Thus, features of main body portion 100 may eliminate or limit a need for separate components to house and support button 350 and connections thereof or connecting thereto.

One or more features such as dividing portions 360, 362 (see FIG. 8) may protrude into second chamber 304 for purposes of maintaining certain components in certain areas of main body portion 100. For example, tubing, such as air/water and suction tubing, may pass between dividing portion 360 and an external wall formed by main body portion 100 and/or cover portion 300.

Main body portion 100 may also include a proximal neck portion 370. Proximal neck portion 370 may include one or more ridges 372 and one or more grooves 374. Ridges 372 and grooves 374 may mate with complementary portions of a sleeve 380. For example, sleeve 380 may have one or more grooves 382 that may mate with ridges 372 of neck portion 370 and may have one or more ridges 384 that mate with grooves 374 of neck portion 370. Stress relief portion 26 may fit over neck portion 370 (and, therefore, sleeve 380). Sleeve 380 may serve to channel components such as wires, tubing, etc. from an operation portion 12 to umbilicus 24.

FIG. 9 shows a second side cover portion 300 that has been removed from a second side 16 of operation portion 12, shown in FIG. 8. Cover portion 300 may be connectable to a second side 106 of main body portion 100 by holes or recesses 381 in body portion 100 and holes or recesses 382 in cover portion 300. Cover portion 300 may fit over second chamber 304 and may fully or partially enclose second chamber 304 from an exterior of main body portion 100. A mechanism such as a screw, pin, bolt, or other connector may be used to join holes or recesses 381 to holes or recesses 382. Additionally or alternatively, other mechanisms may be used for joining cover portion 300 to main body portion 100. For example, cover portion 300 may snap onto main body portion 100 or otherwise attach to main body portion, including, for example, by glue, welding, or other adhesives. Cover portion 300 may include one or more protruding support portions 390, 392, which may provide support to circuit board 340. Support portions 390, 392, together with support portions 330, 332 of main body portion 100, may keep a circuit board 340 in an intended location and may prevent or minimize unintended movement of circuit board 340. A wall of cover portion 300 may include curved concave portions 394 and 396 that have complementary shapes to curved concave portions 320, 322 of main body portion 100 and/or bodies of valves 52 and 54. Bodies of valves 52 and 54 may have a same or similar radius of curvature as concave portions 394 and 396. Together, curved concave portions 320 and 396 may form a secure casing around valve 52, and curved concave portions 322 and 394 may form a secure casing around valve 54.

Cover portion 300 may also include a cover neck portion 400 that may have the same shape as or a complementary shape to a neck portion 370 and that may align with neck portion 370 when cover portion 300 is secured to main body portion 100. Cover neck portion 300 may have one or more ridges 402 that may have any of the properties of ridges 372 and may interact with groove 382. Cover neck portion 300 may also include one or more grooves 404 that may have any of the properties of grooves 374 and that may interact with ridges 384. As with neck portion 370, stress relief portion 26 may fit over cover neck portion 400. Together, neck portion 370 and cover neck portion 400 may have a circular cross-section and/or may form a tubular shape.

As can be seen by referring to FIGS. 5 and 8, certain components of operation portion 12 of device 10 may pass from second chamber 304 into first chamber 116, and vice versa. For example, wires or tubes for passing suction, air, and/or water may pass from second chamber 304 into first chamber 116. For example, suction tube 410 may pass from second chamber 304 into first chamber 116. Although other tubes are not shown in FIG. 5 for purposes of clarity of illustration, air and/or water tubes may also pass into first chamber 116. First chamber 116 and second chamber 304 may be in fluid communication with one another. Features such as dividing portions 360, 362 may assist in aligning components such as tubes or wires to pass from second chamber 304 to first chamber 116 in a desired location. For example, dividing portions 360, 262 may constrain a tube or wire to a desired position. Dividing portions 360, 362 may be disposed at an opening between first chamber 116 and second chamber 304.

The aspects described herein may provide numerous benefits. For example, manufacturing efficiencies may result from a reduced number or complexity of parts, as well as a decreased cost of materials. Furthermore, the structure of main body portion 100 may enable streamlining of manufacture by allowing assembly of a first side 14 and a second side 16 of operation portion 12 to proceed separately. For example, components may first be placed in one of first side 14 or second side 16 and then in the other of first side 14 or second side 16. It may be preferable to first install components in second side 16. After components are installed for a given side 14, 16, respective first cover portion or second cover portion 300 may be secured. Main body portion 100, in conjunction with the other aspects of device 10 described above, may also serve to segregate components of device 10 that could interfere with one another. For example, features of main body portion may prevent liquids or other fluids from interfering with electronic components. Features of main body portion 100 may also maintain wires such as articulation wires 130 in a desired location and prevent interference between components such as articulation wires 130, pull wire 134, tubing, or other wires. Such components may need to be kept separate from one another in order to avoid impairment of functions of those components and/or of device 10.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A handle of an endoscope, the handle comprising:
a body portion that includes:
a wall having:
a first side defining a first interior surface facing a first direction, the first interior surface defining at least part of a first chamber and having a first feature configured to support at least a first component of a steering assembly;
a second side opposite the first side and defining a second interior surface facing a second direction opposite the first direction, the second interior surface defining at least a part of a second chamber and having a second feature configured to support at least one fluidic component or electronic component, wherein the first interior surface and the second interior surface are on opposite sides of a portion of the wall shared by the first chamber and the second chamber, the shared portion of the wall being completely interior to the body portion; and
an exterior surface configured for contact by a user of the handle;
wherein the body portion is a one-piece, integral molded component,
wherein the first interior surface is on a first side of a longitudinal axis of the body portion, and the second interior surface is on a second side of the longitudinal axis, wherein the body portion further defines a recessed portion proximal of the first chamber and configured to receive at least a second component of the steering assembly, and
wherein the second chamber includes a negative of the recessed portion.

2. The handle of claim 1, wherein a second wall of the body portion surrounds the recessed portion, and wherein the second wall has at least a curved portion and a straight portion.

3. The handle of claim 1, wherein the recessed portion defines a first recessed portion and a second recessed portion, wherein the second recessed portion is within the first recessed portion, wherein the second recessed portion is recessed from the first recessed portion, and the second recessed portion is configured to receive at least a third component of the steering assembly.

4. The handle of claim 1, wherein the second chamber has a third feature configured to support at least one valve body.

5. The handle of claim 4, wherein a third wall of the second chamber includes a concave portion configured to surround at least a portion of the valve body.

6. The handle of claim 1, wherein the second feature is configured to support at least one electronic component, wherein the electronic component is a circuit board, and wherein the second chamber has a third feature configured to support a button that is operatively connected to the circuit board.

7. The handle of claim 1, wherein the first chamber and the second chamber are in fluid communication with one another.

8. The handle of claim 7, wherein a passage between the first chamber and the second chamber includes a feature configured to constrain a tube or a wire passing between the first chamber and the second chamber.

9. A handle of an endoscope, the handle comprising:
a main body portion defining a first chamber and a second chamber and being a one-piece, integral molded component, wherein the first chamber is open on one side of a longitudinal axis of the main body portion, and wherein the second chamber is open on a second, opposite side of the longitudinal axis of the main body portion, and wherein a first side of a wall of the main body portion includes a first interior surface facing a first direction and defining at least part of the first chamber, a second side of the wall incudes a second interior surface facing a second direction opposite the first direction and defining at least part of the second chamber, and an exterior surface of the main body portion is configured for contact by a user of the handle, wherein the first interior surface and the second interior surface are on opposite sides of a portion of the wall shared by the first chamber and the second chamber, the shared portion of the wall being completely interior to the body portion;
a component of a steering assembly disposed in the first chamber;
at least one of a fluidic component or an electronic component disposed in the second chamber;
a first cover over the first chamber; and
a second cover over the second chamber.

10. The handle of claim 9, wherein the first chamber includes a first feature configured to support the component of the steering assembly, and wherein the second chamber includes a second feature configured to support the at least one of the fluidic component or the electronic component.

11. The handle of claim 9, wherein the component of the steering assembly is a first component of the steering assembly, and wherein the main body portion define a recessed portion proximal of the first chamber and configured to receive at least a second component of the steering assembly.

12. The handle of claim 9, wherein the at least one of the fluidic component and the electronic component is the electronic component, and the handle further comprises a button operatively connected to the electronic component, and wherein the second chamber includes a feature configured to support the button.

13. The handle of claim 9, wherein the first chamber and the second chamber are in fluid communication with one another, the first cover is attached to the main body portion to enclose the first chamber, and the second cover is attached to the main body portion to enclose the second chamber.

14. The handle of claim 13, wherein the main body portion includes a concave portion, wherein the second cover includes a concave portion, wherein the concave portion of the second cover is complementary to the concave portion of the main body portion.

15. A handle of an endoscope, the handle comprising:
a body portion that includes:
an exterior surface configured for contact by a user of the handle;
a first wall having a first side including a first interior surface facing a first direction and defining at least part of a first chamber configured to receive at least one steering component of a steering assembly, wherein the first chamber defines a recessed portion; and
the first wall having a second side including a second interior surface facing a second direction opposite the first direction and defining at least part of a second chamber configured to receive at least one of a fluidic component and an electronic component, wherein the first interior surface and the second interior surface are on opposite sides of a portion of the first wall shared by the first chamber and the second chamber, the shared portion of the first wall being completely interior to the body portion;
wherein the first interior surface and the second interior surface are on opposite sides of a longitudinal axis of the body portion, and wherein the body portion is a one-piece, integral molded component; and
wherein the second chamber includes a negative of the recessed portion of the first chamber, wherein the recessed portion of the first chamber defines a first recessed portion and a second recessed portion, wherein the second recessed portion is recessed from the first recessed portion, wherein the at least one steering component includes an axle, wherein the second recessed portion receives the axle and constrains rotational movement of a base of the axle.

16. The handle of claim 15, wherein the first chamber includes a first feature configured to support the component of the steering assembly, and wherein the second chamber includes a second feature configured to support the at least one of the fluidic component and the electronic component.

17. The handle of claim 16, wherein the second chamber includes a third feature configured to support at least one valve body.

* * * * *